United States Patent
Hirano

(10) Patent No.: US 6,447,445 B1
(45) Date of Patent: Sep. 10, 2002

(54) ENDOSCOPIC INSERTION INSTRUMENT

(75) Inventor: Sota Hirano, Omiya (JP)

(73) Assignee: Fuji Photo Optical Co., Ltd., Omiya (JP)

( * ) Notice: Subject to any disclaimer, the term of this patent is extended or adjusted under 35 U.S.C. 154(b) by 117 days.

(21) Appl. No.: 09/661,445

(22) Filed: Sep. 13, 2000

(30) Foreign Application Priority Data

Sep. 14, 1999 (JP) ............................................. 11-259802

(51) Int. Cl.[7] .................................................. A61B 1/00
(52) U.S. Cl. ...................................... 600/129; 600/130
(58) Field of Search .............................. 600/129, 128, 600/130, 127, 160

(56) References Cited

U.S. PATENT DOCUMENTS

| | | | | |
|---|---|---|---|---|
| 4,173,392 A | * | 11/1979 | Ekinaka et al. ............ 264/1.28 |
| 4,616,631 A | * | 10/1986 | Takahashi .................... 600/139 |
| 4,826,280 A | * | 5/1989 | Hiramoto et al. ........... 385/116 |
| 4,947,827 A | * | 8/1990 | Opie et al. ................... 600/108 |
| 5,257,617 A | * | 11/1993 | Takahashi .................... 600/123 |
| 5,438,975 A | * | 8/1995 | Miyagi et al. ............... 600/109 |
| 5,876,329 A | * | 3/1999 | Harhen ......................... 600/121 |
| 5,944,654 A | * | 8/1999 | Crawford ..................... 600/128 |

* cited by examiner

*Primary Examiner*—John P. Leubecker
(74) *Attorney, Agent, or Firm*—Oblon, Spivak, McClelland, Maier & Neustadt, P.C.

(57) ABSTRACT

An insertion instrument for an endoscope is disclosed which comprises, a hard end portion formed at least an illuminating means having an illumination lens provided in a lens barrel and light guide, and an observing means at least an objective optical system disposed within an objective lens barrel, the hard end portion being divided into a holding member and a cover member detachably fitted to said holding member, concave shaped recesses provided therebetween for inserting at least the illuminating lens barrel and the objective lens barrel from outer periphery of the holding member inwardly in the radial direction, wherein said recesses have a arc shaped portions to substantially coincide with outer diameters of the illuminating lens barrel and said objective lens barrel, and detachable positioning means provided for positioning the illuminating lens barrel and the objective lens barrel in the recesses in the axial direction.

6 Claims, 7 Drawing Sheets

ENDOSCOPIC INSERTION INSTRUMENT

BACKGROUND OF THE INVENTION

1. Field of the Invention

The present invention relates to an endoscopic insertion instrument, and more particularly relates to the insertion instrument formed to have a small diameter.

2. Description of the Prior Art

An endoscope for medical use generally comprises an operation unit connected to an insertion instrument for inserting into body cavity, etc. and a universal cord to be connected from the operation unit at least to a light source unit. The insertion instrument comprises, from the side of the distal end in order, a hard end portion, an angle portion, and a flexible portion. The hard end portion is provided with at least illuminating means and observing means. In addition to these means, the hard end portion is also provided an channel for inserting treating tools such as forceps therethrough.

The illuminating means includes a light guide and a lens for illumination disposed so as to face the emitting end of the light guide. The lens for illumination is attached within a lens barrel of the illumination lens and the emitting side of the light guide is inserted into the lens barrel of the illumination lens by a predetermined length. The observing means has an objective optical system and at the image forming position of the objective optical system is placed a solid-state imager such as a CCD is arranged or the incidence end of an image guide faces. An optical element including at least one objective lens of the objective optical system is attached within an image lens barrel. The solid-state imager is fixed to the image lens barrel. When using the image guide, the incident side thereof is connected to the image lens barrel. The channel for inserting treating tools is formed of a flexible tube and its fore end is fitted to a hard pipe.

In the hard end portion, through-holes are formed for inserting the above-mentioned illuminating means, observing means, and channel for inserting treating tools. The illuminating lens barrel, the objective lens barrel, and the pipe for inserting treating tools are passed through these through-holes. In such a manner, the illuminating lens barrel, the objective lens barrel, and the pipe for inserting treating tools are fixed to the through-holes formed at the hard end portion. Among various fixing methods, there is firstly a joining method using an adhesive, etc. As to at least the objective lens barrel, a fixing method that set screws are threaded on the side face of the hard tip portion so as to press the set screws against the external peripheral surface of the objective lens barrel is generally adopted.

Of the above-mentioned fixing methods of the illuminating lens barrel, the objective lens barrel, and the pipe for inserting treating tools, the direct fixing by means of the adhesive, etc. causes difficulty in disassembling these members after they are fixed. Therefore, there is a problem that repairs and replacement of these members are extremely troublesome or partial repairs thereon cannot be occasionally performed. Another fixing the objective lens barrel with the set screws enables easily repairs and parts replacement of the observing means. However, the fixing method with set screws has a problem that the external diameter of the hard end portion increases by the dimension required for fixing the set screws. In particular, when the external diameter of the insertion instrument must be extremely reduced in order to insert it into a small-diameter coeliac tract, set screws cannot be used practically for the fixing's sake.

SUMMARY OF THE INVENTION

In view of these problems, the present invention has been made, and it is an object thereof to fix each of members to be attached to an insertion instrument to a hard end portion of the insertion instrument so as to be easily detachable manner without particularly increasing the diameter of the hard end portion.

It is another object of the present invention that in an endoscope having a small-diameter insertion instrument, at least an illuminating lens barrel and an objective lens barrel to be attached to the hard end portion are enabled to be detachably fixed in a precisely positioned state.

In order to achieve the above-mentioned objects, according to the present invention, an insertion instrument for an endoscope which comprises: a hard end portion; an illuminating means fixed to the hard end portion having at least an illuminating lens attached within an illuminating lens barrel and a light guide having an emitting end for facing said illuminating lens; an observing means fixed to the hard end portion having at least an objective optical system disposed within an objective lens barrel; the hard end portion being divided into a holding member and a cover member detachably fitted to the holding member; concave shaped recesses provided between the holding member and the cover member for inserting at least the illuminating lens barrel and the objective lens barrel from outer periphery of the holding member inwardly in the radial direction, wherein the recess have a arc shaped portions to substantially coincide with outer diameters of the illuminating lens barrel and the objective lens barrel; and detachable positioning means for positioning the illuminating lens barrel and the objective lens barrel in the recesses in the axial direction.

Preferably, the holding member further comprises a recess for guiding being formed of a treating tool insertion pipe to be fitted into a treating tool channel, and thereby the concave grooves are formed in the holding member at three positions spaced by an angle of approximately 120° so that the illuminating lens barrel, the objective lens barrel, and the treating tool insertion pipe is placed in the concave recess with positioned in the axial direction by the positioning means. There are formed clearances in the abutting portion between the holding member, and the cover member and between the insertion portions and the external peripheral faces of the illuminating lens barrel, the objective lens barrel, and the treating tool pipe. These clearances may be filled with a sealing material so as to maintain airtightness in these inserted portions. In a case where the hard end portion is prefered to be connected to an angle portion consisting of a bendable pipe sequentially and pivotally connecting a predetermined number of angle rings to each other and an outer cover layer formed of a net and an elastic tube for covering the curved pipe, a difference in level is formed at the base end of the holding member for abutting engagement with an angle ring positioned in the end of the curved pipe, whereby the outer cover layer is connected to the cover member and the base end of the cover member is to be abutted to the difference in level in the larger diameter portion of the holding member. Positioning means may be formed of projections respectively formed on the external peripheral faces of, for example, the illuminating lens barrel, the objective lens barrel, and further the treating tool insertion pipe, and concave pits for positioning formed on the respective groove bottom portions of the concave grooves in the holding member so as to be fitted with the respective projections.

The diameters of the illuminating lens barrel, the objective lens barrel, and the treating tool inserting pipe may be substantially the same and the centers of the illuminating lens barrel, the objective lens barrel, and the treating tool insertion pipe may be arranged so that distances from the center of the holding member thereto are substantially the same in the radial direction. Furthermore, the concave grooves formed on the holding member may have cross-sections of substantial a semicircle of the respective outer diameters of the illuminating lens barrel, the objective lens barrel, and the treating tool insertion pipe, and in the cover member, concave grooves having similar semicircular cross-sections may also be formed.

These and other objects, constitutions, and effects of the present invention will become more apparent from the following embodiments of the present invention described with reference to the drawings. Of course the present invention is not understood by limiting to the embodiments.

DESCRIPTION OF THE EMBODIMENTS

Figure 1:
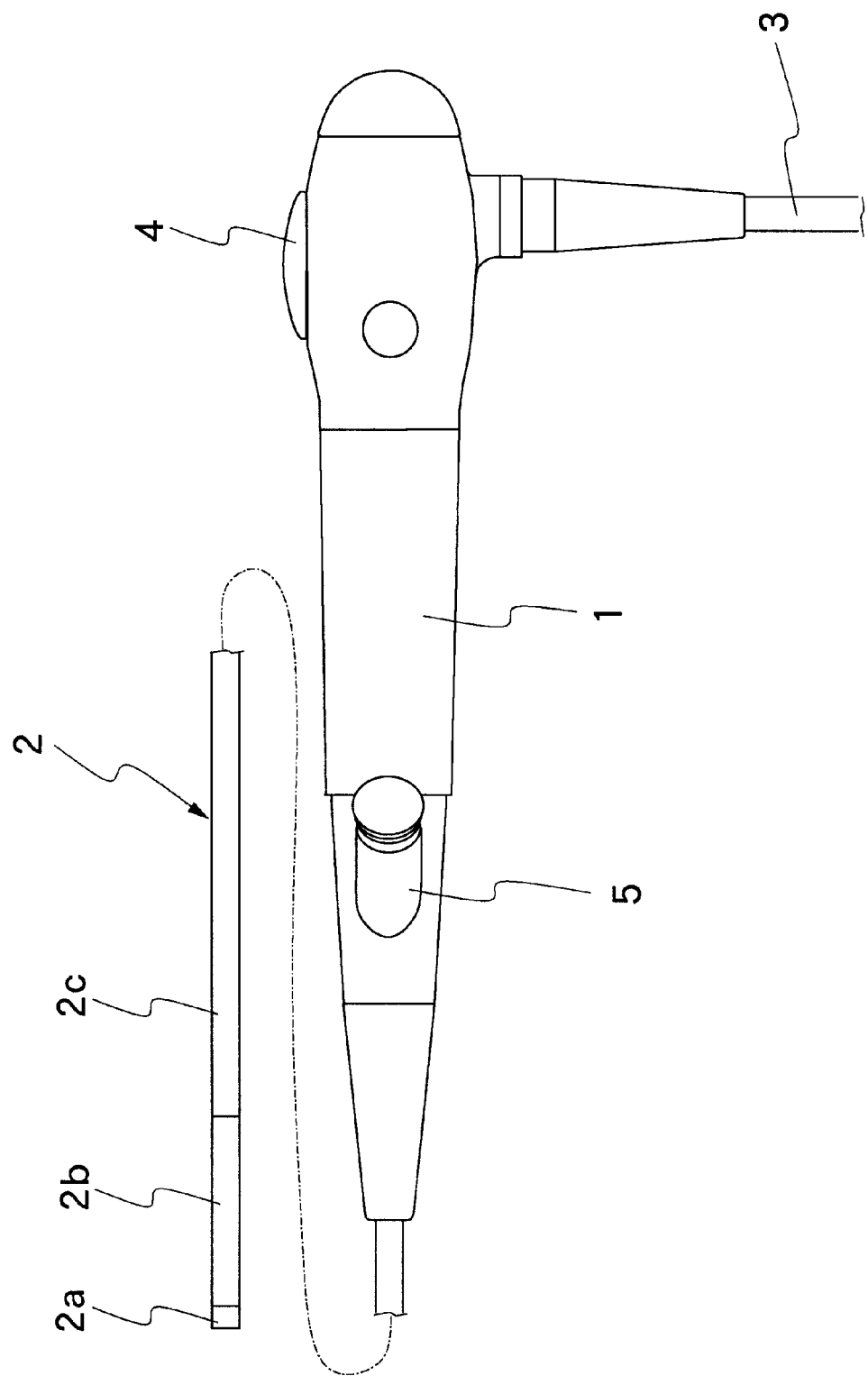
FIG. 1 is an exterior view of an endoscope.
Figure 2:
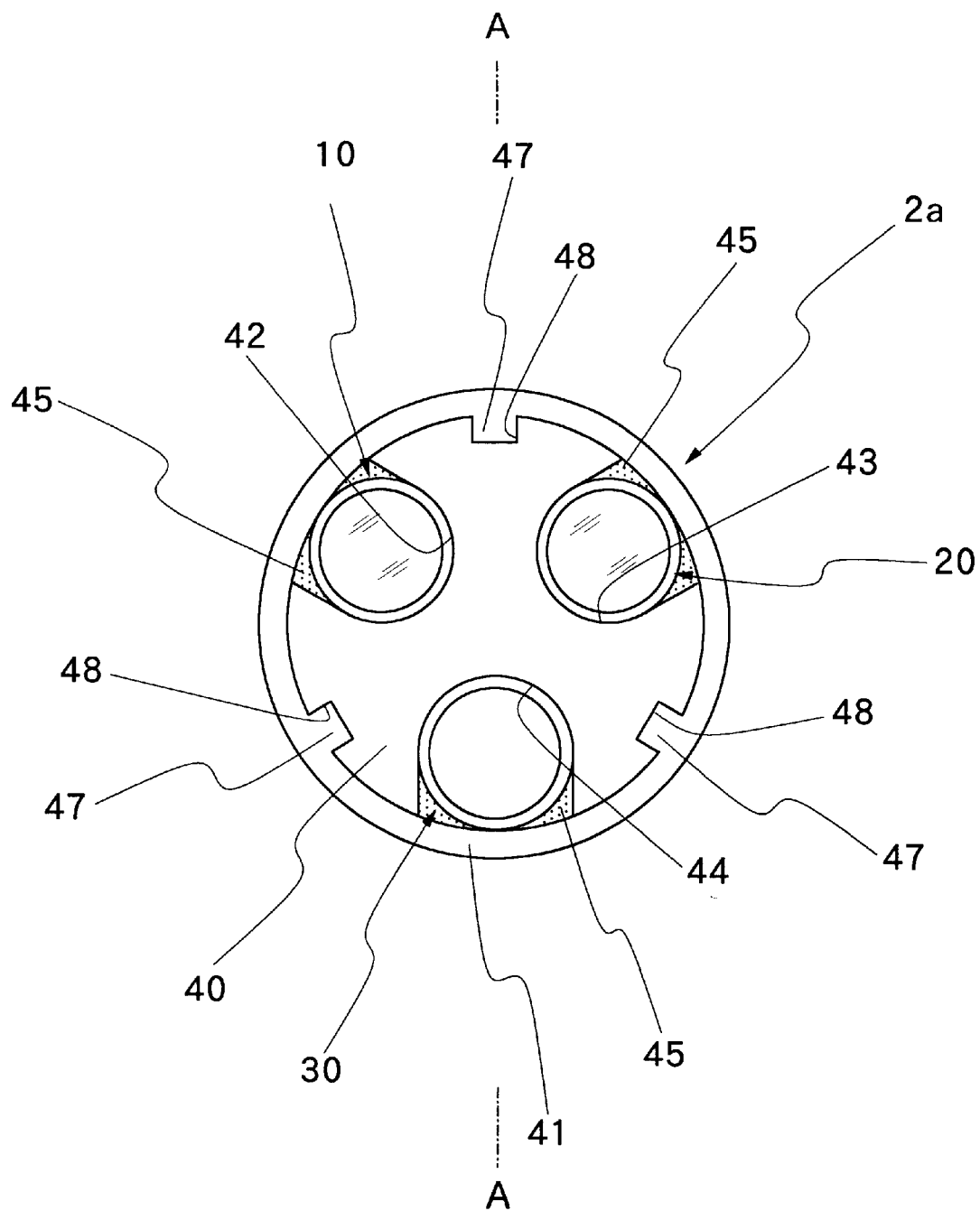
FIG. 2 is a front view of the tip portion of an insertion instrument.

The present invention will be described below with reference to the drawings. FIG. 1 shows the entire structure of an endoscope. In the drawing, reference numeral 1 denotes an operation unit, 2 is an insertion instrument, and 3 denotes a universal cord. The insertion instrument 2 is formed of, from the fore side in order, a hard end portion 2a, an angle portion 2b, and a flexible portion 2c. As shown in FIG. 2, an illuminating means 10, an observing means 20, and a guiding means 30 for treating tools are arranged on the fore-end surface of the hard end portion 2a. The flexible portion has a bendable structure capable of being distorted in an arbitrary direction along an inserting route into a body cavity, etc., forming greater length from a connecting portion to the operation unit. The angle portion 2b is remotely controlled to be distorted by operating angling means 4 provided on the operation unit 1. Thereby, the hard end portion 2a can be oriented in a desired direction. The guiding means 30 is also provided for guiding a treating tool such as a forceps. However, the guiding means is not essentially necessarily provided. In addition, a fluid pipe for supplying a cleaning fluid for cleaning a surface of a lens forming the observing means 20, etc., may be also arranged.

Figure 3:
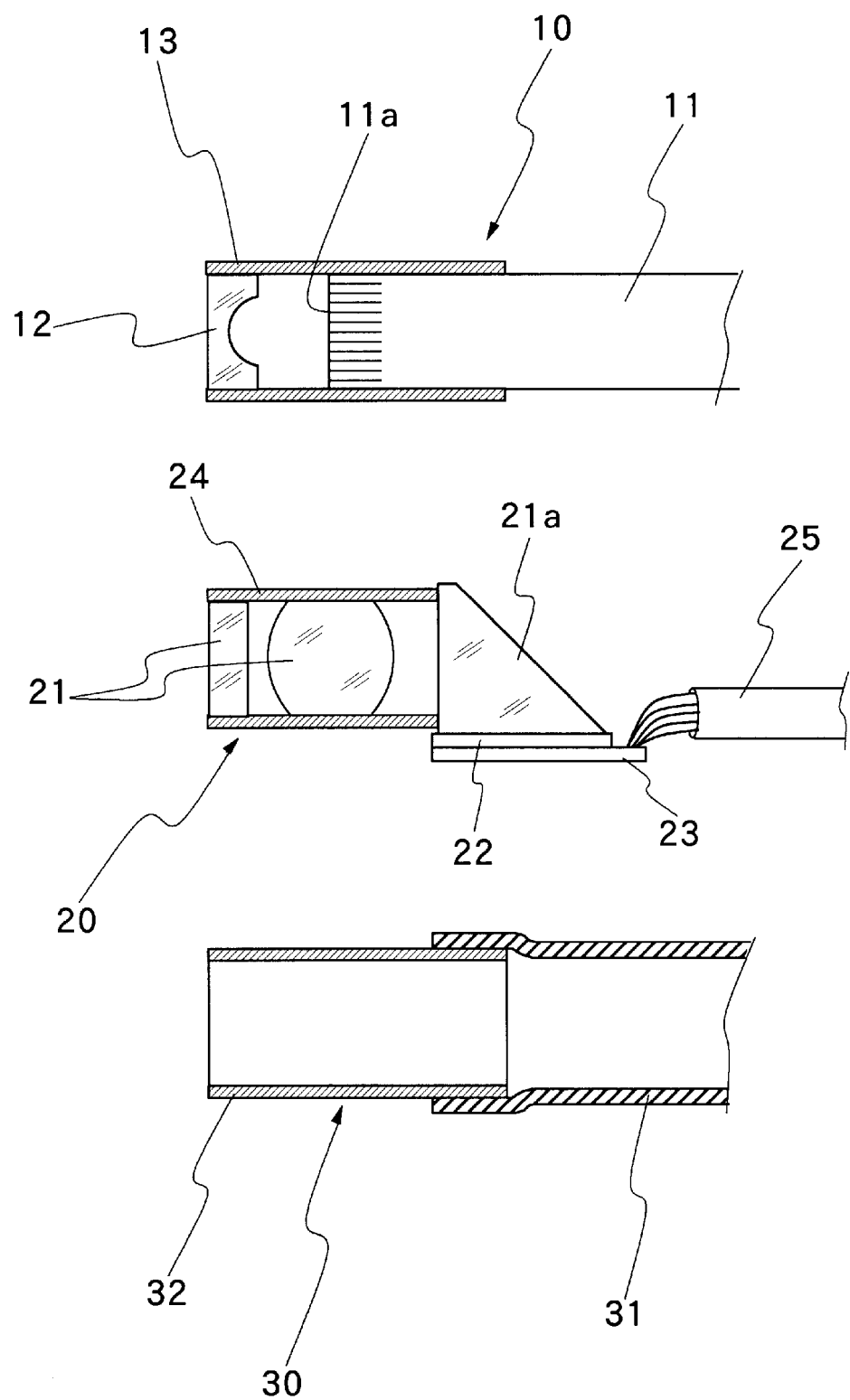
FIG. 3 includes sectional views of essential parts of illuminating means, observing means, and guiding means of treating tools forming intra-endoscopic inserting members.

Then the specific structures of the illuminating means 10, the observing means 20, and the guiding means for treating tools 30 are shown in FIG. 3. Hereinafter, the illuminating means 10, the observing means 20 and the guiding means for treating tools 30 are called generically as an intra-endoscopic inserted member.

The illuminating means 10 comprises a light guide 11 formed of an optical fiber bundle as transmitting means of illuminating light and a lens for illuminating 12 (diverging lens) arranged so as to oppose an emitting end face 11a of the light guide 11. The lens for illuminating 12 is fitted into and to be fixed to an end portion of a illuminating lens barrel 13. The emitting end face 11a of the light guide 11 is inserted into the illuminating lens barrel 13 and spaced from the lens for illuminating 12 by a predetermined distance. The light guide 11 is extended from the insertion instrument 2 into the universal cord 3 via the operation unit 1 to a connector for light-source unit (not shown) arranged at the end of the universal cord 3, enabling illuminating light from a lamp built in the light-source unit to be transmitted.

The observing means 20 comprises an objective optical system 21 having a prism 21a disposed at a midpoint of an optical path of the objective optical system 21 so as to bend the optical path by an angle of 90° and a solid-state imager 22 arranged at an image forming position on the optical path. The solid-state imager 22 is mounted on a substrate 23. The objective optical system 21 is attached within an objective lens barrel 24 having a cover glass or a lens serving as well as a cover glass. The prism 21a is securely disposed on the other end face of the objective lens barrel 24. The solid-state imager 22 is adhered to the prism 21a. Cables 25 are extended from the substrate 23 of the solid-state imager 22. The cables 25, just like the light guide 11, is inserted into the universal cord 3 from the operation unit 1 so as to be detachably connected to a processor (not shown) As the observing means 20, an image guide may also be used instead of the solid-state imager 22. In this case, the image guide is arranged so that an ocular portion is attached in the operation unit 1 and an incidence end of the image guide is arranged at an image forming position of the objective optical system 21 while an emitting end thereof faces the ocular portion having an eyepiece attached thereto.

Furthermore, the guiding means for treating tools 30 is used for performing an appropriate treatment, for ezample, a medical treatment of a diseased part, by inserting a treating tool such as a forceps or a radio-frequency treating tool into a coelom by using the endoscope as its guide means. The guiding means 30 is composed of a treating tool insertion channel 31 formed of a tube material having flexibility in the bending direction and a treating tool inserting pipe 32 formed of a hard pipe such as a metallic pipe being fitted and fixed at the fore end of the insertion channel 31. The treating tool inserting channel 31 is extended toward the vicinity of a connecting portion to the insertion instrument 2 of the operation unit 1 and connected to a treating tool lead-in portion 5 disposed at this position.

Figure 4:
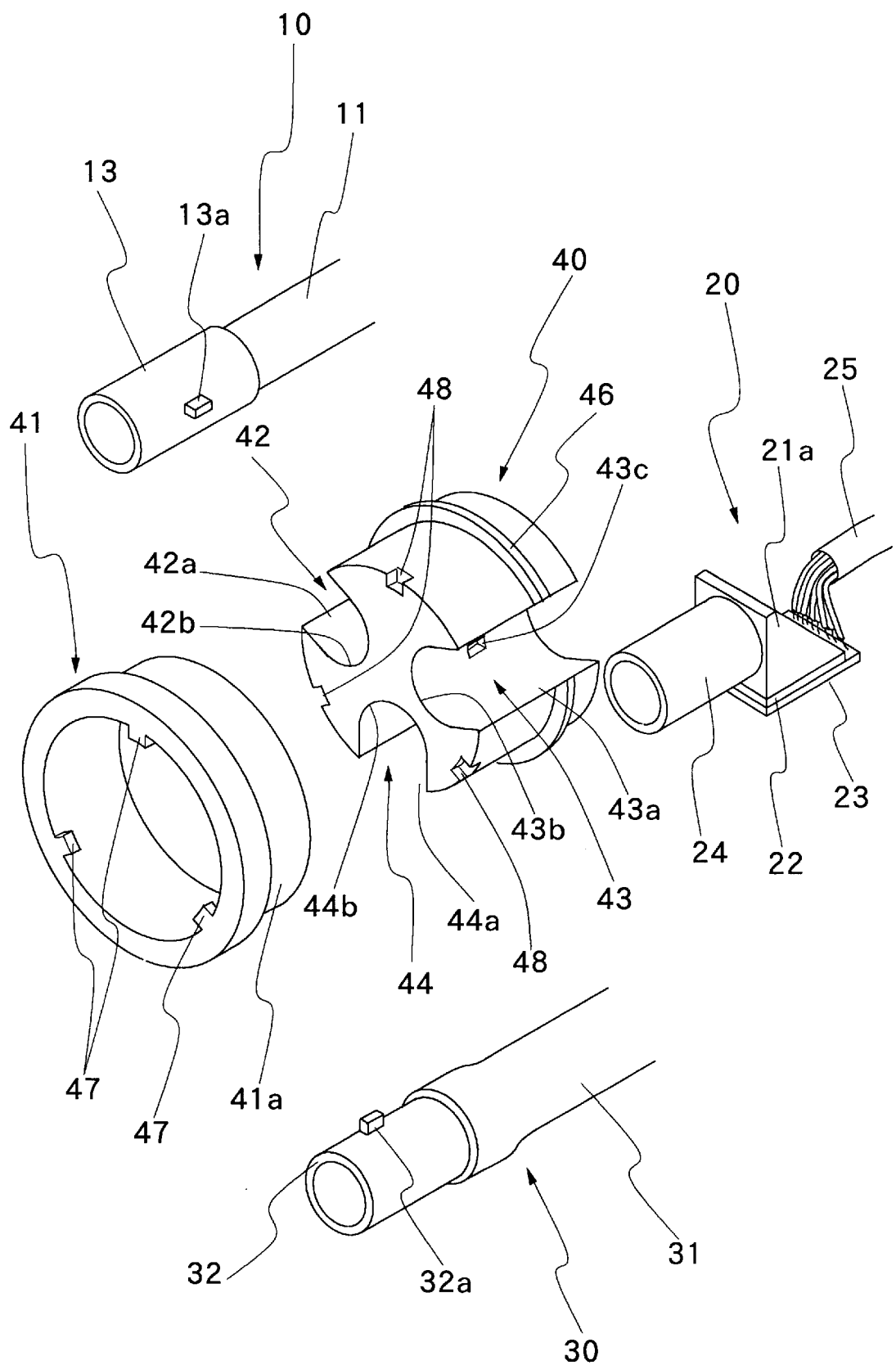
FIG. 4 is an assembly view of a tip structure showed together with each of the intra-endoscopic inserting members.
Figure 5:
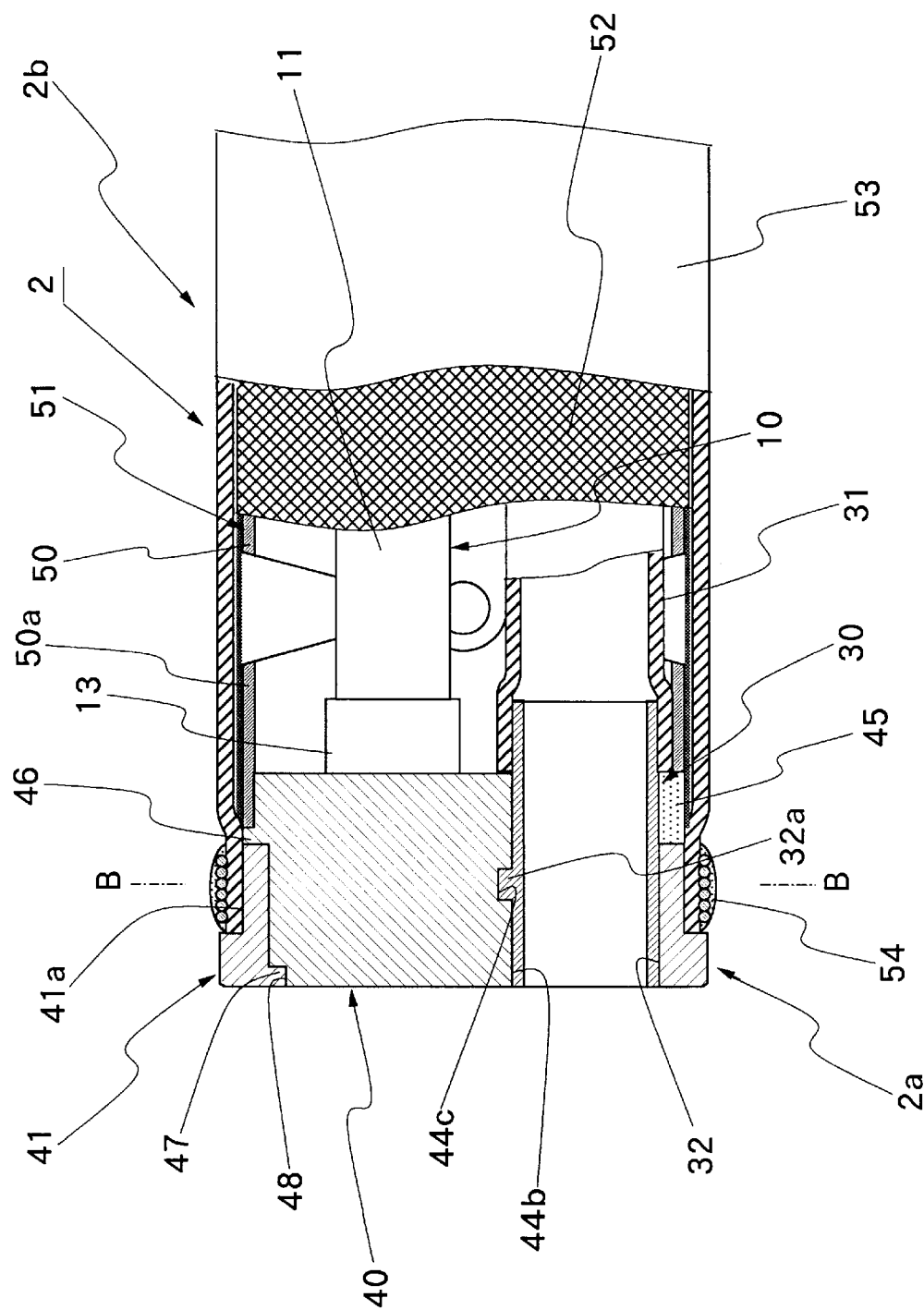
FIG. 5 is a sectional view at the line A—A of FIG. 2.
Figure 6:
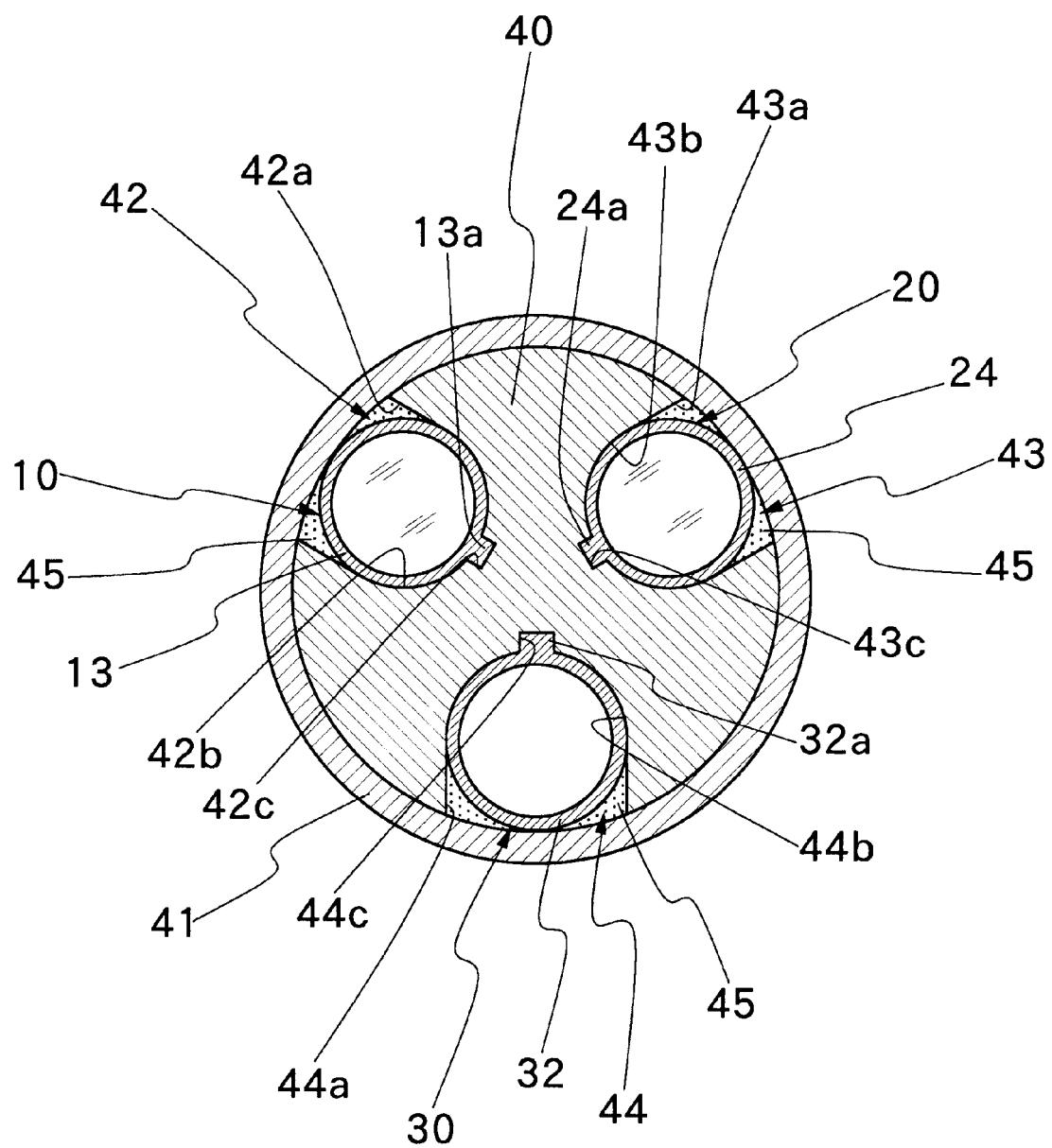
FIG. 6 is a sectional view at the line B—B of FIG. 5.

The distal end portion of the intra-endoscopic inserted member consists of the illuminating means 10, the observing means 20 and the guiding means 30, that is the illuminating lens barrel 13, the objective lens barrel 24, and the treating tool inserting pipe 32, is fixed to the hard end portion 2a. A structure of the hard end portion 2a and a connecting structure thereof to the angle portion 2b are shown in FIGS. 4 to 6.

The hard end portion 2a is formed of a holding member 40 and a cover member 41 both of which are made of a metal, a plastic or the like. Concave-shaped recess 42, 43, and 44 are formed on at three positions in the holding member 40 from the peripheral face side thereof toward inside in the radial direction. The illuminating lens barrel 13, the objective lens barrel 24, and the treating tool inserting pipe 32 are respectively fitted into the recesses 42, 43, and 44. The recesses 42, 43, and 44 have openings for introductory part 42a, 43a, and 44a having the same respective widths as or slightly larger than diameters of the illuminating lens barrel 13, the objective lens barrel 24, and the treating tool inserting pipe 32 and receptors 42b, 43b, and 44b having substantially the same respective curvatures as those of the illuminating lens barrel 13, the objective lens barrel 24, and the treating tool inserting pipe 32. The illuminating lens barrel 13, the objective lens barrel 24, and the treating tool inserting pipe 32 are to be inserted through the respective recesses 42 to 44 from the outside in the radial direction of the holding member 40, and the recesses 42 to 44 function as inserting portions for each of members. In the state accommodated these members, as shown in FIG. 6, the illuminating lens barrel 13, the objective lens barrel 24, and the treating tool inserting pipe 32 are placed so as not to be protruded from the external diameter of the holding member 40 and to be positioned substantially to agree with the external diameter of the holding member 40.

As described above, the illuminating lens barrel 13, the objective lens barrel 24, and the treating tool inserting pipe 32 are respectively accommodated into the recesses 42 to 44 of the holding member 40. In the accommodated state, these members should be positioned at a predetermined position in the axial direction of the hard end portion 2a, that is a position at that end faces of these members agree substantially with the end face of the hard end portion 2a. For this purpose, on the external surfaces of the illuminating lens barrel 13, the objective lens barrel 24, and the treating tool inserting pipe 32, positioning projections 13a, 24a, and 32a are respectively formed. In the bottom portions of the receptors 42b to 44b in the recesses 42 to 44, positioning pits 42c to 44c are formed so as to be respectively fitted with the projections 13a, 24a, and 32a in a substantially tight manner. Therefore, by the projections 13a, 24a, and 32a and the pits 42c to 44c, positioning means is formed for positioning the illuminating lens barrel 13, the objective lens barrel 24, and the treating tool inserting pipe 32 in the axial direction relative to the holding member 40, and furthermore these members are detachable relative to the holding member 40.

In the state that the illuminating lens barrel 13, the objective lens barrel 24, and the treating tool inserting pipe 32 are respectively accommodated in the recesses 42 to 44 of the holding member 40, the cover member 41 is fitted to the external peripheral surface of the holding member 40. Consequently, the illuminating lens barrel 13, the objective lens barrel 24, and the treating tool inserting pipe 32 are completely fixed to the hard end portion 2a. That is, the illuminating lens barrel 13, the objective lens barrel 24, and the treating tool inserting pipe 32 are restricted in the axial direction by fitting of the positioning projections 13a, 24a, and 32a into the positioning pits 42c to 44c, while being restricted in a direction orthogonal to the axial direction by the cover member 41. There are formed clearances between the external peripheral surfaces of the illuminating lens barrel 13, the objective lens barrel 24, and the treating tool inserting pipe 32, the internal surfaces of the recesses 42 to 44 of the holding member 40, and the internal face of the cover member 41. However, these clearances are filled with a sealing material 45.

As understood from FIG. 5, the angle portion 2b is formed of a bendable pipe 51 formed by arranging a predetermined number of angle rings 50 so as to connect to each other pivotally, a net 52 woven with metallic wires covering the external peripheral surface of the bendable pipe 51, and an outer elastic cover layer 53 formed of a rubber tube and the like for covering the external face of the net 52. The holding member 40 forming the hard end portion 2a is fitted into the tip portion of an end ring 50a of the angle rings 50 forming the bendable pipe 51. The fore end of the outer cover layer 53 in the angle portion 2b is fitted to the base end side of the cover member 41 by a predetermined width. In the portion of the base end side of the holding member 40, an annular rib 46 is projectingly formed, and the end face of the end ring 50a forming the bendable pipe 51 is fitted so as to abut the rising face of the rib 46. In a portion of the base end side of the cover member 41, to which the end of the outer cover layer 53 is fitted, an annular groove 41a is formed, and the tip end of the outer cover layer 53 abuts the rising portion of the annular groove 41a and is securely stuck with a thread winding 54 and an adhesive in a position within the annular groove 41a. Furthermore, in the tip internal periphery of the cover member 41, stopper protruding portions 47 oriented inwardly are formed at three positions so as to be engaged with stopper receiving portions 48 formed between the recesses in three positions.

The outer cover layer 53 forms the external surface of the angle portion 2b, and when the angle portion 2b is curved during the angle operation, the outer cover layer 53 is partially expanded and contracted. Forming the outer cover layer 53 of a rubber tube enables this expansion and contraction to be performed. Furthermore, to prevent wrinkles on the outer cover layer 53, a tension is to be exerted on the outer cover layer 53 in the fitting state. Thereby, a force is normally exerted on the cover member 41 connecting to the outer cover layer 53 in a direction leading toward the angle portion 2b. Consequently, a stopper projection 47 formed in the cover member 41 urges in contact with a stopper receiver 48 of the holding member 40, and further the annular rib 46 formed in the holding member 40 is urged in contact with the end ring 50a in the bendable pipe 51. Accordingly, the holding member 40 and the cover member 41, both forming the hard end portion 2a, are held in a connected state to the angle portion 2b, while the holding member 40 is stationary fitted into the cover member 41 maintaining the relative position therebetween.

Due to the structure described above, the tip end portion of each intra-endoscopic inserted member of the endoscopic insertion instrument 2 of the endoscope is detachably fixed to the hard end portion 2a. That is, the illuminating lens barrel 13, the objective lens barrel 24, and the treating tool insertion pipe 32 are respectively arranged so as to face an illuminating window 4, an observing window 5, and exit of the treating tool 6 on the end face of the hard end portion 2a, while the light guide 11 with the emitting end face 11a inserted into the illuminating lens barrel 13, the cable 25 from the solid-state imager 22 attached to the end face of the objective lens barrel 24, and the treating tool insertion channel 31 connected to the treating tool inserting pipe 32 are extended to required positions from the inside of the insertion instrument 2. Since in these intra-endoscopic inserted members, the projections 13a,24a, and 32a respectively formed in the illuminating lens barrel 13, the objective lens barrel 24, and the treating tool insertion pipe 32 engage the positioning pits 42c to 44c in a tightly fitted state, while the external peripheral surfaces of these members are substantially in an abutting state to the inner surface of the cover member 41, these members are completely fixed in the axial direction and in the direction orthogonal to the axis. Even if the height of the projections 13a, 24a, and 32a are extremely small, these members can be securely fixed, so that the fixing mechanism of the illuminating lens barrel 13, the objective lens barrel 24, and the treating tool insertion pipe 32 can be formed to be miniaturized and become compact, thereby reducing the diameter of the hard end portion 2a.

Although the hard end portion 2a itself is divided into the holding member 40 and the cover member 41, the holding member 40 is fixed to the end ring 50a of the angle portion 2b, the cover member 41 is fixed to the outer cover layer 53. Then, the cover member 41 is held so as not to move relatively toward the angle portion 2b in a fitting state in the holding member 40 due to the tension on the outer cover layer 53. Further, the stopper projections 47 formed in the tip end portion of the cover member 41 are engaged with the stopper receivers 48 formed in the holding member 40. Furthermore, a pushing force toward the angle portion 2b is exerted on the holding member 40, so that the holding member 40 is urged in contact with the end ring 50a forming the bendable pipe 51 of the angle portion 2b. As a result of this structure, even when an external force from various directions is exerted on the illuminating means 10 of the hard end portion, the observing means 20, and the guiding means 30 disposed on the distal end of the hard end portion, there is no apprehensiveness that these members are displaced or dropped off.

Each intra-endoscopic inserted member can be securely fixed in the placed state. However, assembling and disassembling can be easily performed. For disassembling, the hard end portion 2a is firstly divided from the angle portion 2b by removing the thread winding 54, the cover member 41 can be separated from the outer cover layer 53.

As described above, after separating the hard end portion 2a from the angle portion 2b, the cover member 41 forming the hard end portion 2a is separated from the holding member 40. Although the cover member 41 is not movable toward the angle portion 2b relative to the holding member 40, it can be moved toward the opposite, i.e., toward the distal end, thereby the cover member 41 being separated from the holding member 40. Since the clearances between the cover member 41 and the holding member 40 are filled with the sealing material 45, there may be a slight resistance against the separating. However, they can be easily separated without any tool because of no adhesive function. Therefore, during the separating, there is no danger of damaging the cover member 41, the holding member 40, and further the intra-endoscopic inserted members, etc. After separating the cover member 41, the illuminating lens barrel 13, the objective lens barrel 24, and the treating tool insertion pipe 32 can be easily taken out by pulling out them placed in the respective recesses 42 to 44 in the holding member 40 toward the openings for introductory part 42a to 44a. Therefore, repairs and replacement, etc., of these intra-endoscopic inserted members can be easily performed. Although the sealing material 45 adheres to the holding member 40 and the cover member 41, the sealing material 45 can be peeled off by cleaning.

In order to place the intra-endoscopic inserted members into the hard end portion 2a and to connect this hard end portion 2a to the angle portion 2b, the opposite procedure to the above-mentioned one may be followed. That is, the illuminating lens barrel 13, the objective lens barrel 24, and the treating tool insertion pipe 32 are inserted thereinto from the openings for introductory part 42a to 44a of the recesses 42 to 44 in the holding member 40 so that the projections 13a, 24a, and 32a thereof are engaged with the positioning pits 42c to 44c in the recesses 42 to 44. Then cavities and the external peripheral faces of the recesses 42 to 44 are coated with the sealing material 45, and the cover member 41 is fitted into the holding member 40 until a position that an internal face rib 41b of the cover member 41 abuts against the reduced diameter portion 40b in the distal end. The holding member 40 is further connected and stuck to the end ring 50a toward the angle portion 2b while the cover member 41 is fitted into the outer cover layer 53 so as to be fixed with the thread winding 54. Thereby, each intra-endoscopic inserted member can be easily assembled into the hard end portion 2a of the insertion instrument 1.

Figure 7:
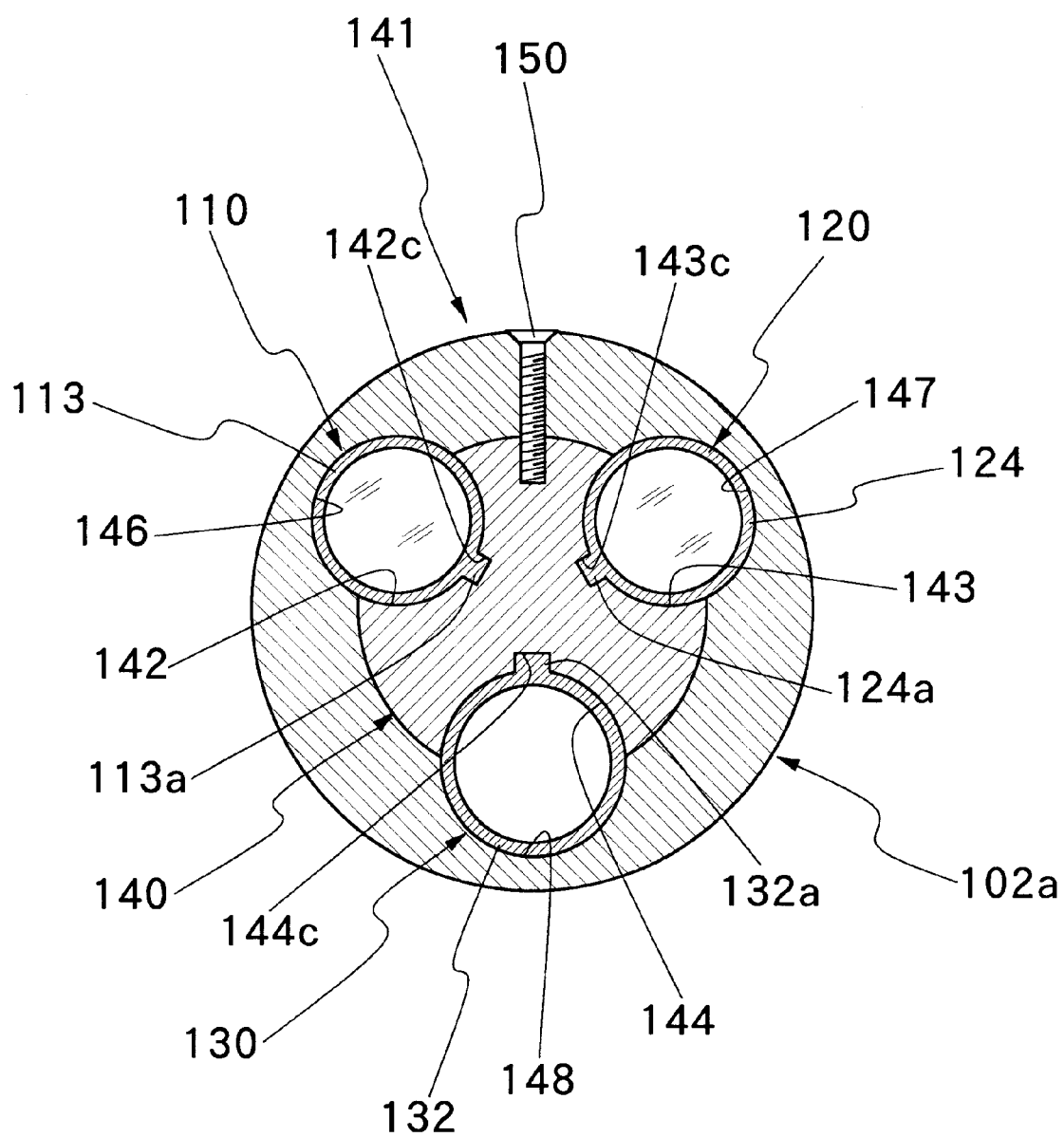
FIG. 7 is a similar sectional view to FIG. 6 showing another embodiment of the present invention.

In the embodiment described above, the recesses are formed only the external peripheral surface of the holding portion while the internal peripheral surface of the cover member is cylindrical. However, as shown in FIG. 7, a distal end structure 102a may be formed of a holding member 140 having semicircular recesses 142, 143, and 144 formed on the external peripheral surface thereof and a cover member 141 having semicircular recesses 146, 147, and 148 formed on the internal peripheral surface thereof. On the bottoms of the recesses 142, 143, and 144 in the holding member 140, positioning pits 142c, 143c, and 144c are formed so as to be respectively engaged with projections 113a, 124a, and 132a formed on the respective external peripheral faces of a illuminating lens barrel 113, an objective lens barrel 124, and a treating tool inserting pipe 132. Therefore, by fitting the holding member 140 into the cover member 141, three through-holes are formed of the recesses 142, 143, and 144 and the recesses 146, 147, and 148, respectively with semicircular cross-sections. In this state, a set screw 150 is inserted through the cover member 141 so as to be threaded into the holding member 140, so that the holding member 140 can be fixed in the connected state to the cover member 141. Accordingly, the cover member 141 is connected to the angle portion and the holding member 140 is fixed to the cover member 141.

Due to the structure described above, just like the above-mentioned first embodiment, the fore end portion of each intra-endoscopic inserted member can be detachably fixed to a hard end portion 102a. Moreover, the fixing is performed by bringing the positioning pits into engagement with the projections, so that the fixing mechanism can be formed to be miniaturized and to become compact, thereby reducing the diameter of the hard end portion 102a. The placing portions of the illuminating lens barrel 113, the objective lens barrel 124, and the treating tool inserting pipe 132 forming illuminating means 110, observing means 120, and guiding means for treating tools 130 have minimum clearances, so that internal airtightness can be secured without a sealing material or with a small amount of the sealing material when using it.

Since three inserting through portions having circular cross-sections are formed of the recesses 142, 143, and 144 and the recesses 146, 147, and 148, respectively having semicircular cross-sections; the centers of these inserting through portions must be located at least in positions spaced by the same distances from the center of the holding member 140. For example, when the diameters of all the inserting through portions are equalized while the diameters of the illuminating lens barrel 113, the objective lens barrel 124, and the treating tool inserting pipe 132 are the same as the diameter of the inserting through portion, and the inserting through portions are located to be spaced by an angle of 120°, the processing of the holding member 140 and the cover member 141 becomes easy, and moreover the insertion and withdrawal of the illuminating lens barrel 113, the objective lens barrel 124, and the treating tool inserting pipe 132 are easily performed.

What is claimed is:

1. An insertion instrument for an endoscope which comprises:

a hard end portion;

an illuminating means fixed to said hard end portion having at least an illuminating lens attached within an illuminating lens barrel and a light guide having an emitting end for facing said illuminating lens;

an observing means fixed to said hard end portion having at least an objective optical system disposed within an objective lens barrel;

said hard end portion being divided into a holding member and a cover member detachably fitted to said holding member;

concave shaped recesses provided between said holding member and said cover member for inserting at least said illuminating lens barrel and said objective lens barrel from an outer periphery of said holding member inwardly in the radial direction, wherein said recesses have arc shaped portions to substantially coincide with outer diameters of said illuminating lens barrel and said objective lens barrel; and detachable positioning means for positioning said illuminating lens barrel and said objective lens barrel in said recesses in the axial direction.

2. An insertion instrument according to claim 1, wherein said hard end portion further comprises a recess for inserting a treating tool guide means, said treating tool guide means being formed of a treating tool insertion pipe to be fitted into a treating tool insertion channel, whereby three recesses are formed in said holding member spaced by an angle of approximately 120° so that said illuminating lens barrel, said objective lens barrel, and said treating tool insertion pipe are fitted in said recesses an positioned in their axial directions by respective positioning means.

3. An insertion instrument according to claim 2, wherein a sealing material is filled within an abutting portion between said holding member and said cover member, and within clearances between insertion portions and said external peripheral faces of said illuminating lens barrel, said objective lens barrel, and said treating tool insertion pipe.

4. An insertion instrument according to claim 2, wherein said positioning means are formed of projections formed on respective external peripheral faces of said illuminating lens barrel, said objective lens barrel, and said treating tool insertion pipe, and positioning pits formed on said respective bottom portions of the recesses so as to be fitted with the respective projections.

5. An insertion instrument according to claim 2, wherein the centers of said illuminating lens barrel, said objective lens barrel, and said treating tool insertion pipe are located such that their centers have substantially the same distance from the center of said holding member in the radial direction, said recesses formed on said holding member having cross-sections in the form of semicircles having substantially respective outer diameters similar to said illuminating lens barrel, said objective lens barrel, and said treating tool insertion pipe, and recesses having similar semicircular cross-sections also being formed on the inner surface of said cover member, and a screw is threaded therethrough so as to fix said cover member to said holding member in a fitting state therebetween.

6. An insertion instrument according to claim 1, wherein said hard end portion is connected to an angle portion, said angle portion being formed of a bendable pipe sequentially and pivotally connecting a predetermined number of angle rings to each other and an outer cover layer formed of a net and an elastic tube for covering said bendable pipe, a difference in level is formed in a base end of said holding member for abutting engagement with an angle ring positioned in the fore end of said bendable pipe, said outer cover layer being connected to said cover member, further, a stopper means is formed for keeping said cover member to prevent from passing through said holding member toward said angle portion.

* * * * *